United States Patent
Yi et al.

(10) Patent No.: US 11,170,070 B2
(45) Date of Patent: Nov. 9, 2021

(54) SPARSE COMPONENT ANALYSIS METHOD FOR STRUCTURAL MODAL IDENTIFICATION WHEN THE NUMBER OF SENSORS IS INCOMPLETE

(71) Applicant: Dalian University of Technology, Liaoning (CN)

(72) Inventors: Tinghua Yi, Liaoning (CN); Xiaojun Yao, Liaoning (CN); Hongnan Li, Liaoning (CN)

(73) Assignee: DALIAN UNIVERSITY OF TECHNOLOGY, Liaoning (CN)

( * ) Notice: Subject to any disclaimer, the term of this patent is extended or adjusted under 35 U.S.C. 154(b) by 334 days.

(21) Appl. No.: 16/342,952

(22) PCT Filed: Mar. 6, 2018

(86) PCT No.: PCT/CN2018/078116
§ 371 (c)(1),
(2) Date: Apr. 17, 2019

(87) PCT Pub. No.: WO2019/169544
PCT Pub. Date: Sep. 12, 2019

(65) Prior Publication Data
US 2020/0073908 A1    Mar. 5, 2020

(51) Int. Cl.
*G06F 17/14* (2006.01)
*A61B 5/11* (2006.01)
*A61B 5/00* (2006.01)
*G06F 7/556* (2006.01)
*H04L 29/08* (2006.01)

(52) U.S. Cl.
CPC ............. *G06F 17/14* (2013.01); *A61B 5/11* (2013.01); *A61B 5/7257* (2013.01); *G06F 7/556* (2013.01); *A61B 2562/0219* (2013.01); *H04L 67/12* (2013.01)

(58) Field of Classification Search
CPC ..... B25J 9/1676; B25J 9/1697; G05D 1/0044; G05D 1/0214; G05D 1/0246; G05D 2201/0203; G05D 1/0016; G05D 1/0212; G05D 1/0274; G05D 2201/0215; G05D 1/0219; G05D 1/0248; G05D 2201/0208; A47L 11/4083; A47L 2201/022; A47L 2201/024; A47L 2201/06; A47L 9/009; A47L 9/0472; A47L 9/0477; A47L 9/0686; A47L 9/1409; A47L 9/2857; A47L 9/00; G06K 9/00664; G06K 9/6267; G06K 9/00536; G01C 21/165; G01C 21/206; G01S 15/86; G01S 15/89; G01S 17/89; G01S 17/931; G01S 5/0252; G01S 5/02585; G01S 5/16; G01S 7/4817; G06T 17/05; H04W 16/20; H04W 4/029; H04W 4/38; H04W 64/00; H04W 84/18; A61B 2562/0219; A61B 5/055; A61B 5/11; A61B 5/24; A61B 5/242; A61B 5/245; A61B 5/246; A61B 5/7203; A61B 5/7235; A61B 5/7257; A61K 48/00; C07K 14/705; G06F 17/14; G06F 7/556; H04L 67/12
USPC ......... 340/825.69, 310.16, 825.43, 658, 660, 340/639, 7.25, 3.31
See application file for complete search history.

(56) References Cited

U.S. PATENT DOCUMENTS

| | | | |
|---|---|---|---|
| 7,125,676 B2 * | 10/2006 | George, Jr. .......... | C07K 14/705 435/7.1 |
| 10,433,742 B2 * | 10/2019 | Huang ................. | A61B 5/242 |
| 2020/0217666 A1 * | 7/2020 | Zhang ................. | G01C 21/165 |

FOREIGN PATENT DOCUMENTS

| CN | 104112072 A | 10/2014 |
|---|---|---|
| CN | 105008887 A | 10/2015 |
| CN | 106844935 A | 6/2017 |
| CN | 107133195 A | 9/2017 |

* cited by examiner

*Primary Examiner* — Daniel Previl
(74) *Attorney, Agent, or Firm* — Muncy, Geissler, Olds & Lowe, P.C.

(57) ABSTRACT

Structural health monitoring providing sparse component analysis method for structural modal identification with incomplete number of sensors. Transforming structural acceleration response data into time frequency domain by short time Fourier transform, detecting time frequency points contributed by only one-order mode where real and imaginary parts have the same direction, and taking the detection result as the initial result of single-source-points; refining the initial result of detection of single-source-point located near the peak of power spectral density, and clustering single-source-points to obtain a mode shape matrix; constructing generalized spectral matrixes using short time Fourier transform coefficients, conducting singular value decomposition on generalized spectral matrix at a single-source-point, taking the first singular value as an auto-spectrum of single-order mode, obtaining the frequency of each order by picking the peak of auto-spectrum, and extracting damping ratio of each order by transforming the auto-spectrum into a time domain through inverse Fourier transform. By means of this method, structural modal parameters are obtained when the number of sensors is incomplete, thereby increasing the identification accuracy of the sparse component analysis method.

1 Claim, No Drawings

SPARSE COMPONENT ANALYSIS METHOD FOR STRUCTURAL MODAL IDENTIFICATION WHEN THE NUMBER OF SENSORS IS INCOMPLETE

TECHNICAL FIELD

The present invention belongs to the technical field of data analysis for structural health monitoring, and relates to a method for structural modal identification when the number of sensors is incomplete, whose content is a sparse component analysis method for structural modal identification when the number of sensors is incomplete.

BACKGROUND

Because of being capable of acquiring dynamic characteristics of a structure, modal identification becomes one of the important technologies to obtain structural dynamics. The dynamic characteristics of the structure include frequencies, mode shapes and damping ratios in general. Because the process of identifying modal parameters from vibration data is consistent with the blind source separation method in principle, a modal identification method based on the blind source separation theory arises at the historic moment. For the site test of a large-scale civil engineering structure, because the number of installed sensors is less than the number of modes to be identified sometimes, the study on the problem of underdetermined blind source separation has a very high practical value.

For the problem of underdetermined blind source separation, researchers have already proposed many methods at present. For example, the second-order blind identification method which conducts decomposition by constructed Hankel matrix can reduce requirements for the number of sensors using augmentation of the matrix; and the second-order blind identification method based on the parallel factor decomposition method can keep the uniqueness of matrix decomposition in an underdetermined case, thereby solving the underdetermined problem. However, because these methods are mainly based on decomposition of the correlation matrix of vibration signals, there is a need for the vibration signals to satisfy the assumption of stationarity. The method based on sparse component analysis obtains the mode shape matrix using clustering characteristics of vibration signals in the time frequency domain first, then reconstructs modal response of each order in accordance with the sparse reconstruction method, and obtains frequencies and damping ratios finally. Because it uses the sparse characteristics of the vibration signals in the time frequency domain, there is no need to assume that the signals are stationary, thereby having great superiority.

The sparse component analysis process includes detection of single-source-point, whose objective is to extract the time frequency points contributed by only one-order mode, thereby increasing the accuracy of mode shape estimation and reducing the amount of calculation. However, when the number of sensors is less, the accuracy of detection of single-source-point is relatively low, which may cause relatively low accuracy of mode shape estimation. In addition, for the modal response during sparse reconstruction, less number of available sensors may cause that not all modal responses can be completely reconstructed, thereby causing that the accuracy of reconstruction may be reduced or omitted. Therefore, it is necessary to increase the modal identification accuracy of the sparse component analysis method when the number of sensor is less.

SUMMARY

The objective of the present invention is to provide an improved modal identification method based on sparse component analysis, to increase the modal identification accuracy of the sparse component analysis method when the number of sensors is less.

The technical solution of the present invention is as follows:

A sparse component analysis method for structural modal identification when the number of sensors is incomplete, including transforming structural acceleration response data into into a time frequency domain by conducting short time Fourier transform, detecting time frequency points (i.e. single-source-points) which are contributed by only one-order mode based on the fact that the real part and imaginary part have the same direction, and taking the detection result as the initial result of the single-source-points; refining the initial result of detection of single-source-point in accordance with the fact that single-source-points are located near the peak of power spectral density, and clustering the single-source-points to obtain a mode shape matrix; constructing generalized spectral matrixes using short time Fourier transform coefficients, conducting singular value decomposition on the generalized spectral matrix at a single-source-point, taking the first singular value as an auto-spectrum of a single-order mode, obtaining the frequency of each order by picking the peak of the auto-spectrum, and extracting the damping ratio of each order by transforming auto-spectrum into a time domain through inverse Fourier transform.

The method includes estimating mode shape matrix and extracting frequencies and damping ratios, and the specific steps are as follows:

(I) Estimating Mode Shape Matrix

Step 1: Acquiring an acceleration response $Y(t)=[y_1(t), y_2(t), \ldots, y_l(t)]^T$ of a structure at a time t when the number of sensors is incomplete; transforming an acceleration response of a time domain into a time frequency domain using short time Fourier transform. Then, the expression of the response is changed to $Y(t,\omega)=[y_1(t,\omega), y_2(t,\omega), \ldots, y_l(t,\omega)]$, where l represents the number of sensors, and $\omega$ represents circular frequency;

Step 2: Acquiring and marking an initial result of detection of single-source-point;

The fact that the real part and imaginary part of a time frequency coefficient have the same direction is taken as a basis of detection of single-source-point, using the following formula:

$$\left| \frac{\text{Re}\{Y(t,\omega)\}^T \text{Im}\{Y(t,\omega)\}}{\|\text{Re}\{Y(t,\omega)\}\| \|\text{Im}\{Y(t,\omega)\}\|} \right| > \cos(\Delta\beta),$$

where $\text{Re}\{\bullet\}$ represents the real part of the extracted data, $\text{Im}\{\bullet\}$ represents the imaginary part of the extracted data, and $\Delta\beta$ represents the threshold of detection of single-source-point;

If the detected single-source-point location is marked as $(t_k, \omega_k)$, the value is:

$$Y(t_k,\omega_k)=[y_1(t_k,\omega_k), y_2(t_k,\omega_k), \ldots, y_l(t_k,\omega_k)]^T;$$

Step 3: Averaging logarithmic amplitudes of all sensor locations;

Conducing the same processing on time frequency coefficients of all sensor locations: if the time frequency coefficient of the $j^{th}$ sensor location is $y_j(t,\omega)$, connecting time frequency coefficients $y_j(t,\omega_i)$ corresponding to all frequency sections $\omega_i$, i=1, 2, . . . , N in sequence to obtain sequences $\tilde{y}_j$, where N represents the number of frequency points used in short time Fourier transform;

Averaging the logarithmic amplitudes of all sensor locations: calculating the logarithmic amplitude of each element in each of the sequence $\tilde{y}_j$, j=1, 2, . . . , l using $Amp_j(\tau)=20\times\log_{10}(|\tilde{y}_j(\tau)|)$, where $\tilde{y}_j(\tau)$ represents the $\tau^{th}$ element in the sequence $\tilde{y}_j$, $Amp_j(\tau)$ represents the $\tau^{th}$ element in the logarithmic amplitude of the $j^{th}$ sensor location; and averaging logarithmic amplitudes:

$$Amp_{mean}(\tau) = \frac{1}{l}\sum_{j=1}^{l} Amp_j(\tau),$$

to obtain a mean logarithmic amplitude;

Step 4: Calculating trend items of the mean logarithmic amplitude sequence $Amp_{mean}$ using polynomial regression, and then removing the trend items, to obtain a sequence $\overline{Amp}_{mean}$; conducting statistical analysis on $\overline{Amp}_{mean}$, and calculating the number of samples falling into each statistical interval; when the number of accumulated samples reaches 90% of the total number of samples, setting a sample value of a corresponding statistical interval as a threshold, and marking a time frequency point set represented by samples below the threshold as $\Omega$; removing points falling into the set $\Omega$ in the initial result $Y(t_k,\omega_k)$ of detection of single-source-point obtained in step 2, to obtain refined single-source-points $Y(\hat{t}_k,\hat{\omega}_k)$;

Step 5: Dividing the refined single-source-points $Y(\hat{t}_k,\hat{\omega}_k)$ into categories using hierarchical clustering, and calculating the clustering center of each category, i.e. mode shape matrix;

(II) Extracting Frequency and Damping Ratio

Step 6: Constructing a generalized spectral matrix using the time frequency coefficients $Y(t,\omega)$ in step 1:

$$H_{yy} = E\begin{bmatrix} STFT_{y_1y_1}(t_i, \omega) & STFT_{y_1y_2}(t_i, \omega) & \ldots & STFT_{y_1y_l}(t_i, \omega) \\ STFT_{y_2y_1}(t_i, \omega) & STFT_{y_2y_2}(t_i, \omega) & \ldots & STFT_{y_2y_l}(t_i, \omega) \\ \vdots & \vdots & \ddots & \vdots \\ STFT_{y_ly_1}(t_i, \omega) & STFT_{y_ly_2}(t_i, \omega) & \ldots & STFT_{y_ly_l}(t_i, \omega) \end{bmatrix}$$

where $STFT_{y_jy_k}(t_i,\omega)=y_j(t_i,\omega)\cdot y^*_k(t_i,\omega)$; $t_i$ represents the $i^{th}$ time; superscript * represents the conjugation for determining the complex number; and E[•] represents the expectation for extracting data;

Step 7: If the frequency index contained in the single-source-point location $(\hat{t}_k,\hat{\omega}_k)$ is $\hat{\omega}_k$, conducting singular value decomposition on the generalized spectral matrix $H_{yy}$ at $\hat{\omega}_k$, to obtain a first singular value sequence $s_1$ at each frequency;

Step 8: Taking the value on the first singular value sequence $s_1$ of each category of single-source-points obtained in step 5 as an auto-spectrum of each order of modes, obtaining the frequency each order by picking the peak frequencies of $s_1$, and extracting the damping ratios by transforming $s_1$ into a time domain through inverse Fourier transform.

The present invention has the beneficial effect that: the present invention provides a modal parameter identification method based on sparse component analysis, to increase the accuracy of modal identification when the number of sensors is less by refining results of detection of single-source-point and directly extracting frequencies and damping ratios from time frequency coefficients.

DETAILED DESCRIPTION

The embodiment of the present invention is further described below in combination with the technical solution.

A mass-spring system of three degree-of-freedom is taken, wherein the mass matrix, stiffness matrix and damp matrix are as follows, respectively:

$$M = \begin{bmatrix} 1 & & \\ & 2 & \\ & & 1 \end{bmatrix} \times 10^3,$$

$$K = \begin{bmatrix} 5 & -1 & 0 \\ -1 & 4 & -3 \\ 0 & -3 & -3.5 \end{bmatrix} \times 10^6,$$

$$C = \begin{bmatrix} 2.339 & 0.663 & -0.832 \\ 0.663 & 3.685 & -0.510 \\ -0.832 & -0.510 & 2.362 \end{bmatrix} \times 10^3$$

In the case where Gaussian white noise is used for excitation, and at the sampling frequency is 100 Hz, acceleration time history of two points is sampled.

I. Estimating Mode Shape Matrix (1) Sampling to obtain an acceleration response $Y(t)=[y_1(t), y_2(t)]^T$ of a structure at a time t; transforming an acceleration response Y of a time domain into a time frequency domain using short time Fourier transform, and changing the expression to be $Y(t,\omega)=[y_1(t,\omega), y_2(t,\omega)]$, where $\omega$ represents circular frequency.

(2) Acquiring an initial result of detection of single-source-point in accordance with $$\left|\frac{Re\{Y(t, \omega)\}^T Im\{Y(t, \omega)\}}{\|Re\{Y(t, \omega)\}\|\|Im\{Y(t, \omega)\}\|}\right| > \cos(2°),$$

where Re{•} represents the real part of the extracted data, and Im{•} represents the imaginary part of the extracted data. If the detected single-source-point location is marked as $(t_k,\omega_k)$, the value at the single-source-point is: $Y(t_k,\omega_k)=[y_1(t_k,\omega_k), y_2(t_k,\omega_k)]^T$.

(3) If the time frequency coefficient of the first sensor location is $y_1(t,\omega)$, connecting time frequency coefficients $y_1(t,\omega_i)$ corresponding to all frequency sections $\omega_i$, (i=1, 2, . . . , N) in sequence to obtain sequences $\tilde{y}_1$, and conducting the same processing on $y_2(t,\omega)$; calculating the logarithmic amplitude of each element in each of the sequences $\tilde{y}_j$, (j=1,2) using $Amp_j(\tau)=20\times\log_{10}(|\tilde{y}_j(\tau)|)$, where $\tilde{y}_j(\tau)$ represents the $\tau^{th}$ element in the sequence $\tilde{y}_j$, and $Amp_j(\tau)$ represents the $\tau^{th}$ element in the logarithmic amplitude of the $j^{th}$ sensor location; and averaging logarithmic amplitudes of two sensor locations:

$$Amp_{mean}(\tau) = \frac{1}{2}\sum_{j=1}^{2} Amp_j(\tau),$$

to obtain a mean logarithmic amplitude.

(4) Calculating trend items of the mean logarithmic amplitude sequence $Amp_{mean}$ using polynomial regression, and then removing the trend items, to obtain a sequence $\overline{Amp}_{mean}$; conducting statistical analysis on $\overline{Amp}_{mean}$, and calculating the number of samples falling into each statistical interval; when the number of accumulated samples reaches 90% of the total number of samples, setting a sample value of a corresponding statistical interval as a threshold, and marking a time frequency point set represented by samples below the threshold as $\Omega$; removing points falling into the set $\Omega$ in the initial result $Y(t_k, \omega_k)$ of detection of single-source-point obtained in step (2), to obtain refined single-source-points $Y(\hat{t}_k, \hat{\omega}_k)$.

(5) Dividing the refined single-source-points $Y(\hat{t}_k, \hat{\omega}_k)$ into 3 categories using hierarchical clustering, and calculating clustering center of each category, to obtain a normalized mode shape matrix $$\begin{bmatrix} 0.2190 & 0.9290 & 0.9527 \\ 0.9757 & -0.3700 & 0.3039 \end{bmatrix}.$$

II. Extracting Frequency and Damping Ratio (6) Constructing a generalized spectral matrix using the time frequency coefficients $Y(t, \omega)$ in step (1):

$$H_{yy} = E\begin{bmatrix} STFT_{y_1y_1}(t_i, \omega) & STFT_{y_1y_2}(t_i, \omega) \\ STFT_{y_2y_1}(t_i, \omega) & STFT_{y_2y_2}(t_i, \omega) \end{bmatrix}$$

where $STFT_{y_jy_k}(t_i, \omega) = y_j(t_i, \omega) \cdot y^*_k(t_i, \omega)$; $t_i$ represents the $i^{th}$ time; superscript * represents the conjugation for determining the complex number; and $E[\bullet]$ represents the expectation for extracting data.

(7) Conducting singular value decomposition on the generalized spectral matrix $H_{yy}$ at each frequency index $\hat{\omega}_k$, to obtain a first singular value sequence $s_1$.

(8) Taking the value on $s_1$ of each category of single-source-points obtained in step (5) as an auto-spectrum of each order of modes, obtaining the frequency of each order by picking the peak frequency of $s_1$, and extracting the damping ratio by transforming $s_1$ into time domain through inverse Fourier transform. The frequency identification result is: $f_{n1}$=3.2959 Hz, $f_{n2}$=10.8099 Hz, and $f_{n3}$=11.7813 Hz. The damping ratio identification result is: $\xi_1$=0.0474, $\xi_2$=0.0290, and $\xi_3$=0.0112.

We claim:
1. A sparse component analysis method for structural modal identification when a number of sensors is incomplete, including estimating mode shape matrix and extracting frequencies and damping ratios, wherein the steps are as follows:

estimating mode shape matrix:
step 1: acquiring an acceleration response $Y(t)=[y_1(t), y_2(t), \ldots, y_l(t)]^T$ of a structure at a time t when the number of sensors is incomplete; transforming an acceleration response of a time domain into a time frequency domain using short time Fourier transform; then the expression of the response is changed to $Y(t,\omega)=[y_1(t,\omega), y_2(t,\omega), \ldots, y_l(t,\omega)]$, where l represents the number of sensors, and $\omega$ represents circular frequency;

step 2: acquiring and marking an initial result of detection of single-source-point; the fact that the real part and imaginary part of a time frequency coefficient have the same direction is taken as a basis of detection of single-source-point, using the following formula $$\left|\frac{Re\{Y(t,\omega)\}^T Im\{Y(t,\omega)\}}{\|Re\{Y(t,\omega)\}\|\|Im\{Y(t,\omega)\}\|}\right| > \cos(\Delta\beta),$$

where $Re\{\bullet\}$ represents a real part of the extracted data, $Im\{\bullet\}$ represents the imaginary part of the extracted data, and $\Delta\beta$ represents the threshold of detection of single-source-point; and if the detected single-source-point location is marked as $(t_k, \omega_k)$, the value is:

$$Y(t_k,\omega_k)=[y_1(t_k,\omega_k), y_2(t_k,\omega_k), \ldots, y_l(t_k,\omega_k)]^T;$$

step 3: averaging logarithmic amplitudes of all sensor locations;

conducing the same processing on time frequency coefficients of all sensor locations: if the time frequency coefficient of the $j^{th}$ sensor location is $y_j(t, \omega)$, connecting time frequency coefficients $y_j(t, \omega_i)$ corresponding to all frequency sections $\omega_i$, i=1, 2, . . . , N in sequence to obtain sequences $\tilde{y}_j$, where N represents the number of frequency points used in short time Fourier transform;

averaging the logarithmic amplitudes of all sensor locations: calculating the logarithmic amplitude of each element in each of the sequences $\tilde{y}_j$, j=1, 2, . . . , l using $Amp_j(\tau)=20\times\log_{10}(|\tilde{y}_j(\tau)|)$, where $\tilde{y}_j(\tau)$ represents the $\tau^{th}$ element in the sequence $\tilde{y}_j$, $Amp_j(\tau)$ represents the $\tau^{th}$ element in the logarithmic amplitude of the $j^{th}$ sensor location; and averaging logarithmic amplitudes:

$$Amp_{mean}(t) = \frac{1}{l}\sum_{j=1}^{l} Amp_j(\tau),$$

to obtain a mean logarithmic amplitude;

step 4: calculating trend items of the mean logarithmic amplitude sequence $Amp_{mean}$ using polynomial regression, and then removing the trend items, to obtain a sequence $\overline{Amp}_{mean}$; conducting statistical analysis on $\overline{Amp}_{mean}$; and calculating a number of samples falling into each statistical interval; when the number of accumulated samples reaches 90% of the total number of samples, setting a sample value of a corresponding statistical interval as a threshold, and marking a time frequency point set represented by samples below the threshold as $\Omega$; removing points falling into the set $\Omega$ in the initial result $Y(t_k,\omega_k)$ of detection of single-source-point obtained in step 2, to obtain refined single-source-points $Y(\hat{t}_k,\hat{\omega}_k)$;

step 5: dividing the refined single-source-points $Y(\hat{t}_k,\hat{\omega}_k)$ into categories using hierarchical clustering, and calculating the clustering center of each category, i.e. mode shape matrix;

extracting frequency and damping ratio:

step 6: constructing a generalized spectral matrix using the time frequency coefficients $Y(t,\omega)$ in step 1:

$$H_{yy} = E\begin{bmatrix} STFT_{y_1y_1}(t_i,\omega) & STFT_{y_1y_2}(t_i,\omega) & \ldots & STFT_{y_1y_l}(t_i,\omega) \\ STFT_{y_2y_1}(t_i,\omega) & STFT_{y_2y_2}(t_i,\omega) & \ldots & STFT_{y_2y_l}(t_i,\omega) \\ \vdots & \vdots & \ddots & \vdots \\ STFT_{y_ly_1}(t_i,\omega) & STFT_{y_ly_2}(t_i,\omega) & \ldots & STFT_{y_ly_l}(t_i,\omega) \end{bmatrix}$$

where $STFT_{y_jy_k}(t_i,\omega)=y_j(t_i,\omega)\cdot y^*_k(t_i,\omega)$; $t_i$ represents the $i^{th}$ time; superscript * represents the conjugation for determining the complex number; and E represents the expectation for extracting data;

step 7: if the frequency index contained in the single-source-point location $(\hat{t}_k,\hat{\omega}_k)$ is $\hat{\omega}_k$, conducting singular value decomposition on the generalized spectral matrix $H_{yy}$ at $\hat{\omega}_k$, to obtain a first singular value sequence $s_1$ at each frequency;

step 8: taking the value on the first singular value sequence $s_1$ of each category of single-source-points obtained in step 5 as an auto-spectrum of each order of modes, obtaining the frequencies of each order by picking the peak frequency of $s_1$, and extracting the damping ratios by transforming $s_1$ into a time domain through inverse Fourier transform.

\* \* \* \* \*